(12) United States Patent
Cha et al.

(10) Patent No.: US 10,159,667 B2
(45) Date of Patent: Dec. 25, 2018

(54) COMPOSITION CONTAINING A DPP-IV INHIBITOR FOR PREVENTING OR TREATING RENAL DISEASES

(71) Applicants: DONG-A ST CO., LTD, Seoul (KR); KOREA UNIVERSITY RESEARCH AND BUSINESS FOUNDATION, Seoul (KR)

(72) Inventors: Dae Ryong Cha, Seoul (KR); Young Sun Kang, Seoul (KR); Jin Joo Cha, Seoul (KR); Ji Eun Lee, Seoul (KR); Hyun Wook Kim, Seoul (KR); Mi Hwa Lee, Gyeonggi-do (KR); Jung Eun Kim, Gyeonggi-do (KR); Mi-Kyung Kim, Gyeonggi-do (KR); Moon-Ho Son, Gyeonggi-do (KR); Soon Hoe Kim, Gyeonggi-do (KR)

(73) Assignee: DONG-A ST Co., Ltd, Seoul (KR)

( * ) Notice: Subject to any disclaimer, the term of this patent is extended or adjusted under 35 U.S.C. 154(b) by 0 days.

(21) Appl. No.: 14/392,160

(22) PCT Filed: Jun. 17, 2014

(86) PCT No.: PCT/KR2014/005302
§ 371 (c)(1),
(2) Date: Dec. 23, 2015

(87) PCT Pub. No.: WO2014/208921
PCT Pub. Date: Dec. 31, 2014

(65) Prior Publication Data
US 2016/0184300 A1 Jun. 30, 2016

(30) Foreign Application Priority Data

Jun. 26, 2013 (KR) ........................ 10-2013-0073711

(51) Int. Cl.
*A61K 31/495* (2006.01)
*A61K 45/06* (2006.01)

(52) U.S. Cl.
CPC ............ *A61K 31/495* (2013.01); *A61K 45/06* (2013.01)

(58) Field of Classification Search
CPC .................................................. A61K 31/495
USPC ................................ 514/252.1, 866, 255.01
See application file for complete search history.

(56) References Cited

U.S. PATENT DOCUMENTS

| | | | |
|---|---|---|---|
| 8,440,669 B2 | 5/2013 | Shin et al. | ..................... 514/249 |
| 2011/0201624 A1 | 8/2011 | Shin et al. | ................ 514/255.01 |

FOREIGN PATENT DOCUMENTS

| | | |
|---|---|---|
| CN | 101229373 A | 7/2008 |
| JP | 2011-500508 A | 1/2011 |
| KR | 10-2005-0016452 | 2/2005 |
| KR | 10-2006-0109911 | 10/2006 |
| KR | 10-2010-0042786 | 4/2010 |
| KR | 10-2010-0042786 | 8/2011 |
| KR | 10-2012-0008093 | 1/2012 |
| WO | WO03032965 | * 4/2003 |
| WO | WO 2003/099279 | 12/2003 |
| WO | WO 2005/049022 | 6/2005 |
| WO | WO 2008/130151 | 10/2008 |

OTHER PUBLICATIONS

Haluzik et al., "Renal Effect of DPP-4 Inhibitors: A Focus on Microalbuminuria". International Journal of Endocrinology, vol. 2013, Article ID 895102, pp. 1-7, Jul. 13, 2013.*
Ramos-Nino et al., "Benefits of ACE Inhibitors in Diabetes." Clinical Medicine: Therapeutics, vol. 1, pp. 1041-1051, 2009.*
Cordonnier et al., Role of ACE Inhibitors in Patients with Diabetes Mellitus. Drugs, vol. 61(13), pp. 1883-1892 (Year: 2001).*
Letter/Written Disclosure of the Information Disclosure Statement for the above-referenced application, filed herewith dated Apr. 14, 2016, 2 pages.
English language translation of Chinese Patent Application No. CN 101229373 A, published Jul. 30, 2008, entitled: "Pharmaceutical composition comprising bosentan," 21 pages.
Hocher et al., "Renal and Cardiac Effects of DPP-4 Inhibitors—from Preclinical Development to Clinical Research." Kidney Blood Press. Res. 36:65-84 (2012).
Kang et al., "CCR2 antagonism improves insulin resistance, lipid metabolism, and diabetic nephropathy in type 2 diabetic mice." Kidney International 78(9):883-894 (2010).
Kang et al., "Visfatin is upregulated in type-2 diabetic rats and targets renal cells." Kidney International 78(2):170-181 (2010).
Kim et al., "(2R)-4-oxo-4-β3-(trifluoromethyl)-5,6-dihydro[1,2,4]triazolo[4,3-a]pyrazin-7(8H)-yl]-1-(2,4,5-trifluorophenyl)butan-2-amine: a potent, orally active dipeptidyl peptidase IV inhibitor for the treatment of type 2 diabetes." J Med Chem. 48(1):141-151 (2005).
Kim et al., "Discovery of DA-1229: a potent, long acting dipeptidyl peptidase-4 inhibitor for the treatment of type 2 diabetes." Bioorg Med Chem Lett. 21(12):3809-3812 (2011).
Lee et al., "Effects of Dipeptidyl Peptidase IV Inhibition on Renal Function in Type 2 Diabetic Mice." 2014 Proceeding of the 34th Annual Spring Meeting of the Korean Society of Nephrology 2014(1):172 (2014).
International Search Report and Written Opinion, dated Sep. 12, 2014, in connection with International Patent Application No. PCT/KR2014/005302 [English translation], 10 pages.
Office Action, dated Nov. 2, 2015, in connection with Korean Patent Application No. 10-2014-0073388 [English translation and original document in Korean], 14 pages.

(Continued)

*Primary Examiner* — Barbara P Badio
(74) *Attorney, Agent, or Firm* — Dentons US LLP; Stephanie Seidman

(57) ABSTRACT

The present invention relates to a composition for preventing or treating renal diseases. The composition of the present invention improves lipid metabolism, prevents histological damage including renal fibrosis, alleviates microalbuminuria, and maintains nephrons of renal glomeruli. Therefore, the composition is useful for treating renal diseases.

3 Claims, 14 Drawing Sheets

(56) References Cited

OTHER PUBLICATIONS

International Preliminary Report on Patentability, dated Dec. 29 2015, in connection with International Patent Application No. PCT/KR2014/005302 [English translation], 8 pages.
Letter/Written Disclosure of the Information Disclosure Statement for the above-referenced application, filed herewith dated Sep. 29, 2016, 2 pages.
Examination Report, dated Jul. 18, 2016, in connection with corresponding Australian Patent Application No. 2014299575, 3 pages.
U.S. Appl. No. 14/909,096, filed Jan. 29, 2016, 2016-0176816, Jun. 23, 2016.
Letter/Written Disclosure of the Information Disclosure Statement for the above-referenced application, filed herewith dated Dec. 6, 2016, 2 pages.
Examination Report, dated Nov. 7, 2016, in connection with corresponding Canadian Patent Application No. 2,916,698, 3 pages.
Lettern/Written Disclosure of the Information Disclosure Statement for the above-referenced application, filed herewith dated Jan. 5, 2017, 2 pages.
Extended European Search Report, dated Dec. 6, 2016, in connection with correspondeing European Patent Application No. 14817709.0, 8 pages.
Letter/Written Disclosure of the Supplemental Information Disclosure Statement for the above-referenced application, filed herewith dated Mar. 10, 2017, 2 pages.
Examination Report, dated Jan. 4, 2017, in connection with corresponding Australian Patent Application No. 2014299575, 3 pages.
Letter/Written Disclosure of the Supplemental Information Disclosure Statement for the above-referenced application, filed herewith dated Aug. 25, 2017, 2 pages.
Desai, T. P., "Metformin in Patients with CKD: A new Analysis," Published Mar. 23, 2015 [online], retrieved on Mar. 25, 2017 from: <URL:medscape.com/viewarticle/841720_print, 2 pages.
Pyram et al., "Chronic kidney disease and diabetes," Maturitas 71:94-103 (2012).
Response, submitted Dec. 8, 2016, to Examination Report, dated Jul. 18, 2016, in connection with corresponding Australian Patent Application No. 2014299575, 19 pages.
Response, submitted Apr. 21, 2017, to Examination Report, dated Jan. 4, 2017, in connection with corresponding Australian Patent Application No. 2014299575, 5 pages.
Examination Report, dated May 30, 2017, in connection with corresponding Australian Patent Application No. 2014299575, 4 pages.
Notice of Acceptance, dated Jul. 13, 2017, in connection with corresponding Australian Patent Application No. 2014299575, 3 pages.
Response, submitted May 8, 2017, to Examiner's Report, dated Nov. 7, 2016, in connection with corresponding Canadian Patent Application No. 2,916,698, 18 pages.
Examiner's Report, dated Aug. 17, 2017, in connection with corresponding Canadian Patent Application No. 2,916,698 [D1= KR 10-2010-0042786 A; D2= KR 10-2012-0008093 A], 4 pages.
Response, filed Jun. 15, 2017, to Extended European Search Report, dated Dec. 6, 2016, in connection with European Patent Application No. 14817709.0, 9 pages.
Letter/Written Disclosure of the Supplemental Information Disclosure Statement for the above-referenced application, filed herewith dated Sep. 1, 2017, 3 pages.
The Merck Manual, 18th Edition Japanese Version, Nikkei BP, Inc., 1st Edition 3rd Print, pp. 2131-2134 (2007) [in Japanese].
The Merck Manual, 18th Edition Japanese Version, Nikkei BP, Inc., 1st Edition 3rd Print, pp. 2131-2134 (2007) [English translation], 3 pages.
Office Action, dated Jun. 6, 2017, in connection with corresponding Japanese Patent Application No. 2016-523630 [English translation and original document in Japanese], 8 pages.
Letter/Written Disclosure of the Supplemental Information Disclosure Statement for the above-referenced application, filed herewith dated Jul. 3, 2017, 3 pages.
Examiner's Report, dated Jun. 6, 2018, in connection with Canadian Patent Application No. 2,916,698, 5 pages.

\* cited by examiner

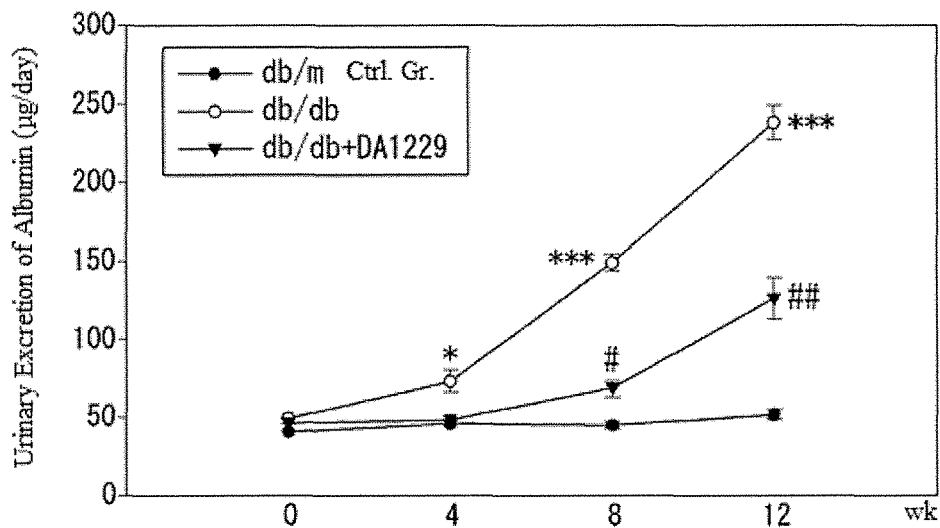
FIG. 6
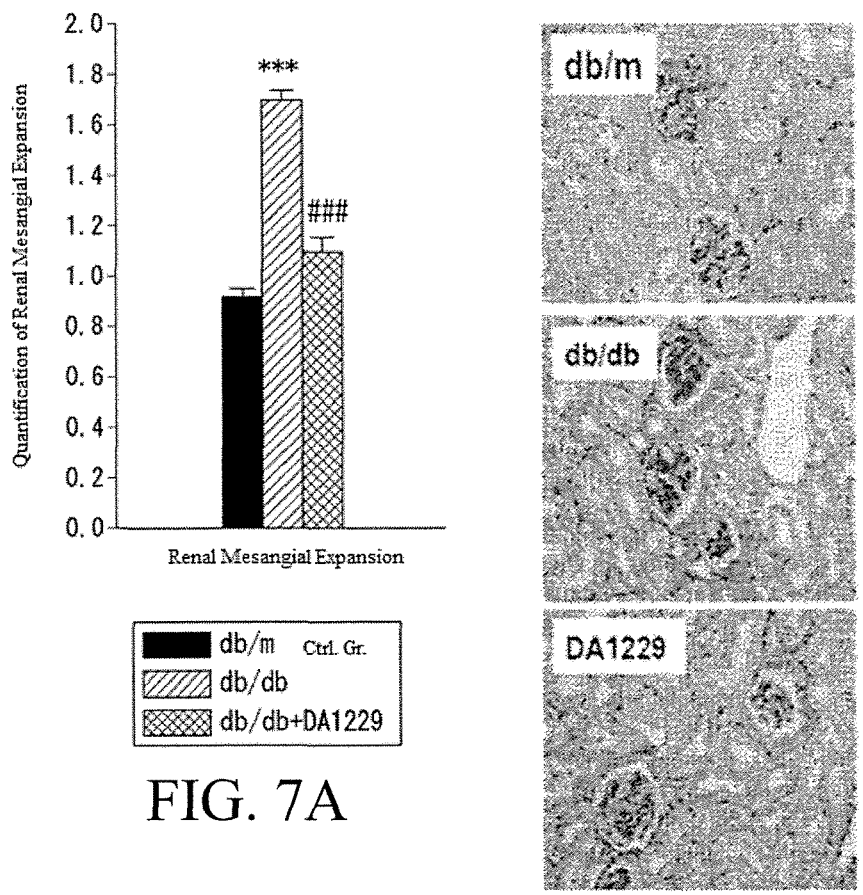
FIG. 7A
FIG. 7B

COMPOSITION CONTAINING A DPP-IV INHIBITOR FOR PREVENTING OR TREATING RENAL DISEASES

RELATED APPLICATIONS

This application is the U.S. National Stage of International Application. No. PCT/KR2014/005302, filed 17 Jun. 2014, which claims benefit of priority to Korean Patent Application KR 10-2013-0073711, filed 26 Jun. 2013, the specification of which is incorporated by reference herein.

TECHNICAL FIELD

The present disclosure relates to a composition for preventing or treating renal diseases.

BACKGROUND

Kidney is an important organ that maintains body homeostasis. It controls body fluid volume, blood ion concentration and pH; secretes waste products such as metabolic wastes, toxin and drug inter alia; and performs blood pressure control, metabolic and endocrine function. Also, it helps calcium absorption in small intestine by activating vitamin D, and it is involved in various hormone synthesis.

Renal disease means a status where overall function of kidney is lowered or abnormalities are incurred due to failure of kidney to perform secretory, control, metabolic and endocrine function normally. Hypofunction caused by kidney injury incurs enlarged kidney and related structures, kidney atrophy, body fluid volume change, electrolyte imbalance, metabolic acidosis, gas exchange disorder, anti-infective function impairment and uremic toxin accumulation inter alia.

Renal diseases are categorized into acute renal failure and chronic renal failure depending on its progression; or into glomerulonephritis due to deposition of vascular complex, diabetic nephropathy accompanied with diabetes or hypertensive renal disease accompanied with hypertension, toxic nephropathy due to drug administration such as antibiotics or anticancer drugs and bacterial infection inter alia depending on cause of the disease.

Irrespective of types of causative renal diseases, when glomerular filtration rate drops below 50% due to chronic progression of renal disorder, in most cases the glomerular filtration rate decreases continuously, end-stage renal failure occurs eventually and may lead to death in severe cases due to complications such as hematological abnormalities, neurological complications, gastrointestinal complications, infection or osteodystrophy inter alia.

Renal diseases are increasing every year worldwide and often discovered when the disease is developed to end-stage renal failure because there are no symptoms or symptoms that are hard to recognize. According to the analysis on the beneficiaries of Medicare that was reported to USRDS (United States Renal Data System), 2.7% of prevalence rate of end-stage renal failure in year 2000 was increased to 8.5% in 2009. In case of South Korea, it was reported that end-stage renal failure patients were 37.1% in total in 2010, which was increased by an annual average of 8.2% compared to that of 2006. These phenomena are closely related to the increase of diabetic nephropathy due to increase of obesity and diabetes patients.

DPP-IV (Dipeptidyl peptidase-IV) is a protein that is also known as adenosine deaminase complexing protein 2 or CD26, and it is encoded by DPP-IV genes. DPP-IV is reported to be involved in immune response, and known as performing an important role in glycometabolism by involving in degradation of GLP-1 (Glucagon-like peptide-1) that promotes insulin secretion and inhibits glucagon secretion. DPP-IV is reported to be dispersed a lot in renal proximal tubule cells, glomerular basement membrane and podocytes. DPP-IV inhibitor has functions of decreasing blood glucose level by inhibiting the degradation of GLP-1 to maintain its activity, and DPP-IV inhibitor is currently being used as an antidiabetic agent because it has no side effects that induce hypoglycemia.

SUMMARY

Technical Problem

The present disclosure provides an effective composition for preventing or treating renal diseases.

Solution to Problem

The present inventors discovered that DA1229, a DPP-IV inhibitor, exhibits effect of preventing or treating renal diseases, and completed the present disclosure.

The present disclosure provides a pharmaceutical composition for preventing or treating renal diseases comprising: a compound represented by Chemical Formula 1 below; its optical isomer; pharmaceutically acceptable salts thereof; or hydrate or solvate thereof as an active ingredient.

[Chemical Formula 1]

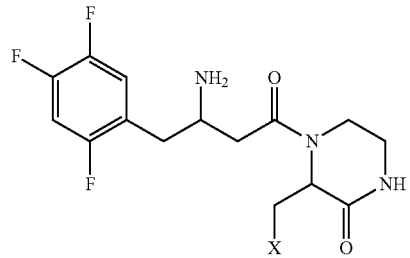

(Wherein, X is $OR^1$ and $R^1$ is $C_1$-$C_5$ lower alkyl group respectively.)

$R^1$ in Chemical Formula 1 can be tert-butyl. The compound is referred to as (R)-4-{(R)-3-amino-4-(2,4,5-trifluorophenyl)butanoyl}-3-(t-butoxymethyl)piperazin-2-one or DA1229, and structure is shown in Chemical Formula 2 below.

[Chemical Formula 2]

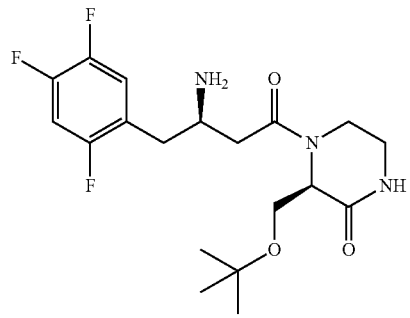

DA-1229

Conventionally, DPP-IV inhibitor has only been recognized as an antidiabetic agent that controls blood glucose but the present inventors confirmed through experiments that DPP-IV inhibitor had direct protective effect on kidney other than effect of blood glucose control, and accordingly completed the present disclosure. DPP-IV inhibitor of the present disclosure decreases lipid concentration of plasma and liver by inhibiting DPP-IV activity and promoting lipid metabolism. Furthermore, DPP-IV has effects of improving renal function; improving microalbuminuria; reducing renal fibrosis; improving nephromegaly; increasing nephrin expression; and inhibiting nephrin excretion. Renal diseases that can be prevented or treated by the composition of the present disclosure include diseases, which exhibits various clinical symptoms induced by various causes; and renal diseases occurs irrespective of diabetes, i.e. non-diabetic nephropathy as well as diabetic nephropathy.

Renal diseases that can be prevented or treated by the composition of the present disclosure could be diabetic nephropathy, glomerulonephritis, hypertensive renal disease, polycystic kidney disease, inflammatory renal disease (glomerulonephritis inter alia), and toxic nephropathy induced by drugs or various toxins inter alia. Clinically, renal disease can be glomerular renal disease that results from abnormal glomerulus associated with proteinuria and tubulointerstitial disease results from abnormal tubule mesangium inter alia in broad terms.

The pharmaceutically acceptable salts of the present disclosure include acetic acid, benzenesulfonic acid, benzoic acid, camphorsulfonic acid, citric acid, ethanesulfonic acid, fumaric acid, gluconic acid, glutamic acid, hydro-bromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluenesulfonic acid and adipic acid inter alia. The pharmaceutically acceptable salts can be selected from a group consisting of acetic acid, citric acid, hydrochloric acid, malic acid, phosphoric acid, succinic acid, tartaric acid and adipic acid but not limited to the above.

The hydrate of the compound of the present disclosure represented by Chemical Formula 1, an optical isomer or pharmaceutically acceptable salts thereof can include stoichiometric or nonstoichiometric amount of water bound by noncovalent intermolecular forces. The hydrate can contain 1 eq. or more of water, preferably 1-5 eq. of water. These hydrate can be prepared by crystallizing the compound represented by Chemical Formula 1 or 2, its optical isomer or pharmaceutically acceptable salts thereof of the present disclosure from water or solvent containing water.

The solvate of the compound of the present disclosure represented by Chemical Formula 1 and an optical isomer or pharmaceutically acceptable salts thereof can include stoichiometric or nonstoichiometric amount of solvent bound by noncovalent intermolecular forces. It is preferable for the solvent to be non-volatile, non-toxic, and the examples of solvents appropriate for human use include ethanol, methanol, propanol and methylene chloride inter alia.

The compound represented by Chemical Formula 1, its optical isomer, pharmaceutically acceptable salts thereof, or hydrate or solvate thereof is DPP-IV (Dipeptidyl Peptidase-IV) inhibitor. DPP-IV inhibitor has an ability to lower blood glucose level by inhibiting the degradation of GLP-1 to maintain its activity.

The pharmaceutical composition of the present disclosure can include other additional active ingredients other than the compound of Chemical Formula 1. The additional active ingredients can have identical or different activity to Chemical Formula 1.

For instance, the additional active ingredients can be antidiabetic drug. Therefore the pharmaceutical composition of the present disclosure can further contain other antidiabetic drugs. The antidiabetic drugs can be selected from a group consisting of biguanide, insulin sensitizer, insulin secretagogue, α-glucosidase inhibitor and cannabinoid receptor 1 antagonist but not limited to the above.

The biguanide of the present disclosure is a drug having effects of promoting anaerobic glycolysis including biguanid structure; enhancing insulin action at peripheral area; inhibiting absorption of glucose from intestine; and inhibiting glyconeogenesis at liver inter alia. The biguanide can be selected from a group consisting of metformin, buformin, phenformin but not limited to the above.

The insulin sensitizer of the present disclosure is a drug acting as decreasing blood glucose level by improving insulin dysfunction, and it is characterized as having TZD (thiazolidin-dione) structure in common. The insulin sensitizer acts on PPAR (Peroxisome Proliferator-activated receptor). The insulin sensitizer can be selected from a group consisting of troglitazone, ciglitazone, rosiglitazone, pioglitazone and englitazone but not limited to the above.

The insulin secretagogue of the present disclosure is a drug promoting insulin secretion of β-cell of pancreas. It can be a drug having sulfonylurea or non-sulfonylurea structure. Preferably, the insulin secretagogue can be: drugs having sulfonylurea structure selected from a group consisting of glybenclamide (also known as glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide and glipentide; or drugs having non-sulfonylurea structure of repaglinide or nateglinide, but not limited to the above.

The α-glucosidase inhibitor of the present disclosure is a drug having a function of inhibiting digestion and absorption of starch and disaccharide inter alia by competitively inhibiting α-glucosidase that is one of intestinal digestive enzymes. The α-glucosidase inhibitor can be selected from a group consisting of acarbose, voglibose, emiglitate and miglitol but not limited to the above.

The cannabinoid receptor-1 antagonist of the present disclosure is a drug controlling glucose and lipid metabolism as well as weight and energy balance by inhibiting excessive activity of endocannabinoid. The cannabinoid receptor 1 antagonist can be selected from a group consisting of rimonabant, otenabant, ibinabant and surinabant but not limited to the above.

Also, for instance, the additional active ingredients of the composition of the present disclosure can be ingredients that can inhibit action of angiotensin. Therefore, the pharmaceutical composition of the present disclosure can further include angiotensin converting enzyme inhibitor or angiotensin II receptor blocker.

The angiotensin converting enzyme inhibitor can be selected from a group consisting of captopril, enalapril, benazepril, imidapril, lisinopril, prinopril, ramipril, moexipril, fosinopril and quinapril but not limited to the above.

The angiotensin II receptor blocker can be selected from a group consisting of candesartan, eprosartan, irbesartan, losartan, telmisartan and valsartan but not limited to the above.

Also, for instance, the additional active ingredients of the composition of the present disclosure can be antihypertensive drugs. Therefore, the pharmaceutical composition of the present disclosure can further include CCB (Calcium Channel Blocker), beta blocker or diuretics but not limited to the above.

The term 'pharmaceutically acceptable' used in the present disclosure is directed to molecular body and other ingredients of compositions that are physiologically acceptable when administered those to mammals including human beings, and that generally do not generate inappropriate responses.

The composition of the present disclosure can further include carriers. The term 'carrier' stated in the present disclosure is directed to diluents, excipients or vehicle, which are administered with active compounds. These pharmaceutical carriers can be: water; saline; aqueous dextrose solution; aqueous glycerol solution; and sterile liquid such as oil including petroleum, animal oil, vegetable oil or synthetic oil such as peanut oil, soybean oil, mineral oil and sesame oil. Proper pharmaceutical carriers are stated in the following reference—"Remington's Pharmaceutical Sciences" by E. W. Martin, 18$^{th}$ Edition. A most preferable carrier for the present disclosure is one performs immediate release, in other words, which releases all or most of active ingredients in a short term such as 60 minutes or less while enabling fast absorption of drugs.

It is preferable for the compound of the present disclosure represented by Chemical Formula 1, its optical isomer, pharmaceutically acceptable salts thereof, or hydrate or solvate thereof to be contained as 0.1-50.0 wt % based on total weight of the composition but not limited to the above. The composition of the present disclosure can be administered in various dosage forms for oral or parenteral administration when it is administered clinically. Diluents or additives such as fillers, extenters, binders, humectants, disintegrants and surfactants inter alia in general use can be used for formulation.

Solid dosage forms for oral administration include tablets, pills, powders, granules and capsules inter alia, and these solid dosage forms can be prepared by adding at least one additive, for example starch, calcium carbonate, sucrose, lactose and gelatin inter alia to the pharmaceutical composition of the present disclosure. Furthermore, lubricants such as magnesium, stearate and talc can also be used.

Liquid dosage forms for oral administration include suspensions, liquid for internal use, emulsions and syrups. Furthermore, various additives such as humectants, sweetening agents, flavoring agents and preservatives other than simple diluents such as water and liquid paraffin can be contained.

Dosage forms for parenteral administration include sterile aqueous solutions, nonaqueous solutions, suspensions, emulsions, lyophilized formulations and suppositories. Propylene glycol, polyethylene glycol, vegetable oils such as olive oil, injectable ester such as ethyl oleate can be used as nonaqueous solvents and emulsions. Witepsol, macrogol, tween 61, cacao butter, laurinum, glycerol and gelatin can be used as base material of the suppositories. The pharmaceutical composition of the present disclosure can be administered subcutaneously, venously or intramuscularly in case of parenteral administration.

Dosage of the pharmaceutical composition of the present disclosure can be adjusted within a range of 0.5 mg to 100 mg a day based on adults weighing 70 kg. However, optimum administration dosage can be easily decided by those skilled in the art and it can be adjusted depending on various factors including: diseases and its severity; contents of active ingredients and other ingredients contained in the composition; types of formulation; patients' age, weight, health, sex, diet; route and time of administration; excretion rate of the composition; treatment period; drugs used simultaneously, inter alia.

The present disclosure provides a method of preventing or treating renal diseases by administering therapeutically effective amount of the compound represented by Chemical Formula 1; its optical isomer; pharmaceutically acceptable salt thereof; or hydrate or solvate thereof to subjects in need of treatment.

The term 'subjects in need of treatment' is directed to mammalia including human beings, and 'administering' is directed to provision of desired substances to patients through any proper methods. The term 'therapeutically effective amount' is directed to an amount of active ingredient or pharmaceutical composition that induces biological or medical responses from animals or human beings, which are considered as so by researchers, veterinarians, doctors or other clinicians. It includes an amount wherethrough alleviation of symptoms of diseases or disorders being treated could be induced. It is obvious to those skilled in the art that the therapeutically effective amount and administration frequency of the active ingredients of the present disclosure can vary depending on desired effects.

The present disclosure provides a use of the compound represented by Chemical Formula 1, its optical isomer, pharmaceutically acceptable salt thereof, or hydrate or solvate thereof in preparation of medicament for treating renal diseases.

Advantageous Effect

The pharmaceutical composition of the present disclosure for preventing or treating renal diseases comprising the compound represented by Chemical Formula 1, its optical isomer, pharmaceutically acceptable salts thereof, or hydrate or solvate thereof as an active ingredient has effects of improving lipid metabolism; preventing histological damages including renal fibrosis; and alleviating microalbuminuria. Therefore, the composition is useful for treating renal diseases.

BRIEF DESCRIPTION OF DRAWINGS

FIG. 6 is a graph showing variation of microalbuminuria after administration of the DPP-IV inhibitor.

FIG. 7A shows a graph showing a result of scoring and FIG. 7B shows the view of renal mesangium enlargement after administration of the DPP-IV inhibitor.

DESCRIPTION OF EMBODIMENTS

Figure 1A:
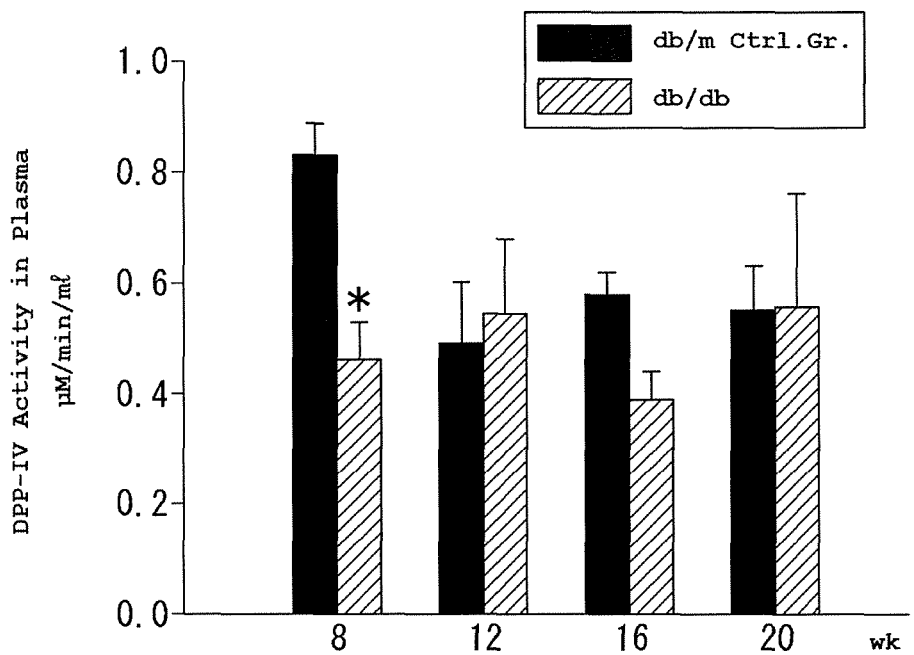
FIGS. 1A and 1B show graphs demonstrating activity variation of DPP-IV in plasma according to stages of diabetes.

The present disclosure will be described more fully hereinafter with reference to the accompanying examples. However, the present disclosure may be embodied in many different forms, and should not be construed as being limited to the embodiments set forth herein.

Furthermore, samples and solvents stated hereinafter were purchased from Sigma-Aldrich Korea unless otherwise specified.

EXAMPLES

<Example 1> Evaluating Weight, Food Intake, Water Intake, Fasting Blood Sugar, Urine Output, Hemoglobin A1c Value and Blood Pressure (1) Preparation of a Non-Diabetic Control Group, Diabetic Group and DA1229 Administration Group 6-week old mice were used. db/m mice were set as the non-diabetic control group (7 for each stage, n=28), and divided db/db mice into the diabetic group (7 for each stage, n=28) and DA1229 administration group (n=8). 0.3% (W/W, 300 mg/kg/day) of DA1229, a DPP-IV inhibitor, was mixed with feed and provided to the DA1229 administration group while only feed was provided to the diabetic group.

(2) Measuring Weight, Food Intake, Water Intake, Fasting Blood Glucose, Urine Output, Hemoglobin A1c Value and Blood Pressure Weight, food intake, water intake, fasting blood glucose, urine output, hemoglobin A1c value (HbA1c) and blood pressure (i.e. systolic blood pressure, SBP) of the non-diabetic control group (db/m control group) and the diabetic group (db/db) were measured at week 0, 4, 8 and 12 of administration; and that of the DA1229 administration group were measured at week 12. HbA1c was measured by using the DCA 2000+ (Bayer Healthcare, Wuppertal, Germany) Analyzer.

Result is shown in Table 1 below.

TABLE 1

| Parameter | wk | db/m Ctrl.Gr. | db/db | db/db + DA1229 |
|---|---|---|---|---|
| Weight (g) | 0 | 24.3 ± 0.5 | 36.1 ± 1.0*** | NA |
|  | 4 | 27.4 ± 1.2 | 47.2 ± 2.0*** | NA |
|  | 8 | 30.7 ± 0.9 | 54.9 ± 1.2*** | NA |
|  | 12 | 33.5 ± 1.1 | 58.9 ± 2.1*** | 57.2 ± 2.5*** |
| Daily Food Intake (g) | 0 | 2.36 ± 0.14 | 5.44 ± 0.34*** | NA |
|  | 4 | 3.36 ± 0.04 | 7.42 ± 0.09*** | NA |
|  | 8 | 3.90 ± 0.15 | 7.15 ± 0.09*** | NA |
|  | 12 | 3.02 ± 0.27 | 6.01 ± 0.03*** | 5.67 ± 0.08*** |
| Daily Water Intake (g) | 0 | 5.5 ± 0.3 | 12.9 ± 0.6*** | NA |
|  | 4 | 4.6 ± 0.2 | 14.8 ± 0.5*** | NA |
|  | 8 | 4.7 ± 0.1 | 15.1 ± 0.0*** | NA |
|  | 12 | 4.1 ± 0.2 | 16.8 ± 0.4*** | 8.6 ± 0.4***,# |
| Fasting Blood Glucose (ml/day) | 0 | 163 ± 15 | 248 ± 13 | NA |
|  | 4 | 190 ± 11 | 472 ± 43*** | NA |
|  | 8 | 168 ± 6 | 458 ± 22*** | NA |
|  | 12 | 153 ± 6 | 562 ± 53*** | 466 ± 66# |
| Urine Output (ml/day) | 0 | 0.30 ± 0.09 | 0.42 ± 0.07 | NA |
|  | 4 | 0.23 ± 0.05 | 1.84 ± 0.28*** | NA |
|  | 8 | 0.19 ± 0.02 | 1.04 ± 0.16* | NA |
|  | 12 | 0.21 ± 0.02 | 1.25 ± 0.36*** | 1.07 ± 0.29** |
| HbA1c(%) | 0 | 3.32 ± 0.84 | 6.18 ± 0.19** | NA |
|  | 4 | 4.56 ± 0.09 | 8.90 ± 0.36*** | NA |
|  | 8 | 4.50 ± 0.18 | 9.90 ± 0.37*** | NA |
|  | 12 | 5.14 ± 0.19 | 9.21 ± 0.43*** | 8.58 ± 0.79*** |
| SBP (mmHg) | 12 | 118 ± 16 | 115 ± 15 | 124 ± 11 |

In Table 1, each value was expressed as mean ± SEM, and statistical analysis was conducted on each group in the same period.
*$P < 0.05$;
**$P < 0.01$;
***$P < 0.001$ vs. db/m control group;
$P < 0.05$ vs. db/db.

Weight was increased; and food intake, water intake, fasting blood glucose, urine output were markedly increased in the diabetic group compared to the non-diabetic control group.

Pertaining to the DA1229 administration group whereto DA1229 was administered for 12 weeks, no significant differences were shown compared to the diabetic group in regard of weight, food intake and urine output. However, water intake and fasting blood glucose were markedly decreased.

It could be understood that DA1229 performs functions of decreasing blood glucose and reducing glucose excretion.

<Example 2> Evaluating DPP-IV Activity

DPP-IV (Dipeptidyl peptidase IV) is an incretin degrading enzyme. Incretin is a hormone that is secreted from small intestine and promotes the secretion of insulin. When DPP-IV activity is inhibited, incretin activity is maintained and insulin secretion is promoted.

Therefore, DPP-IV activities in plasma and each organ were evaluated to confirm whether DPP-IV activity was effectively inhibited by DA1229. The non-diabetic control group, the diabetic group and the DA1229 administration group were prepared in the same manner as Example 1(1), and used for the experiment.

Figure 1B:
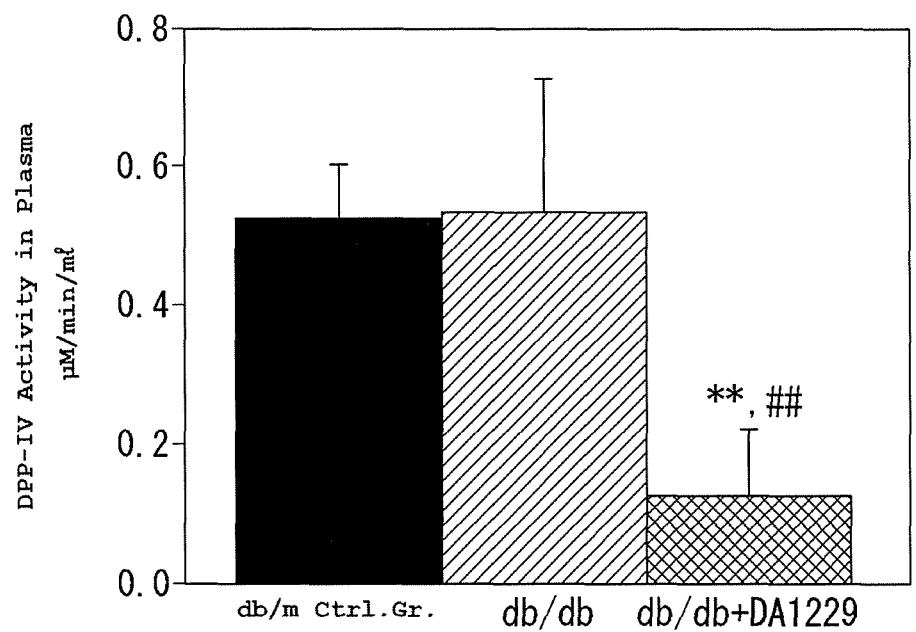
Figure 2A:
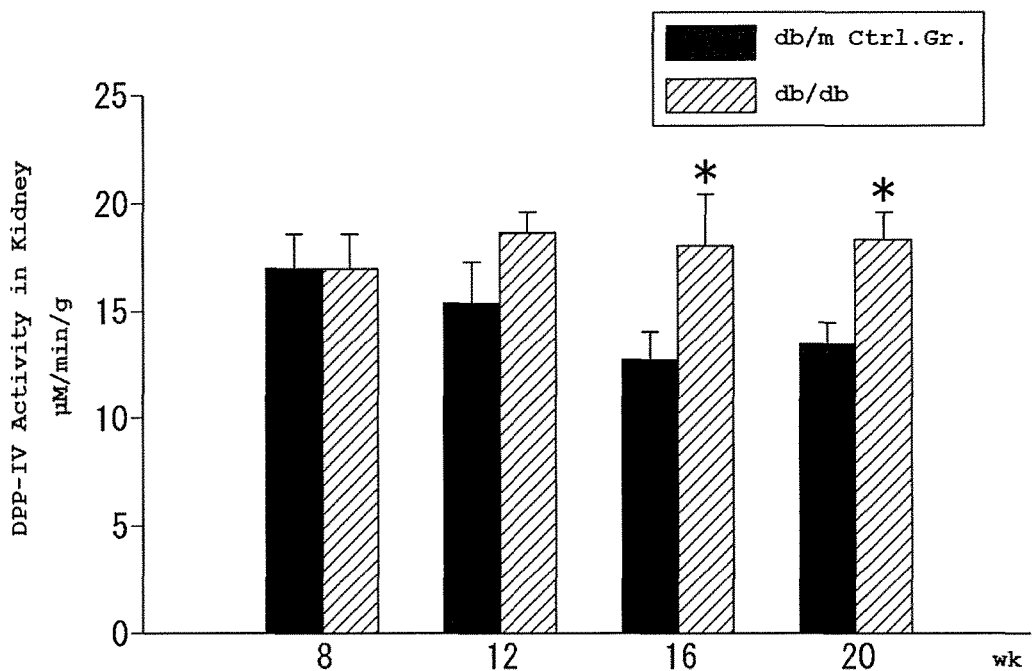
FIGS. 2A-2D show graphs demonstrating activity variation of DPP-IV in kidney (2A), liver (2B), heart (2C) and adipose tissue (2D) according to stages of diabetes.
Figure 2B:
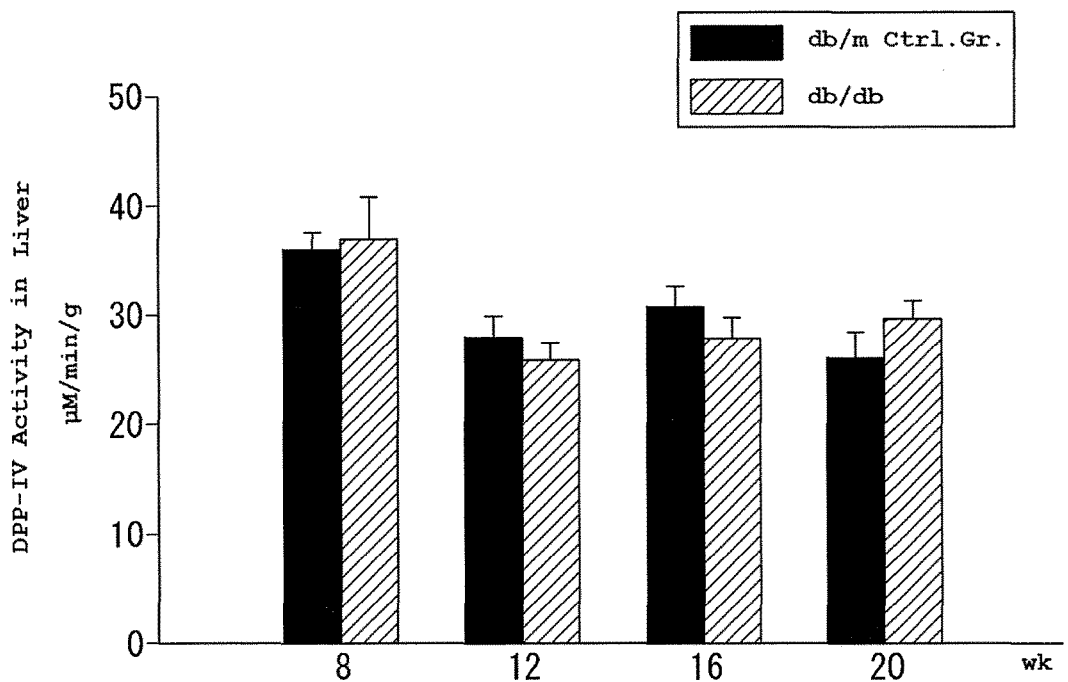
Figure 2C:
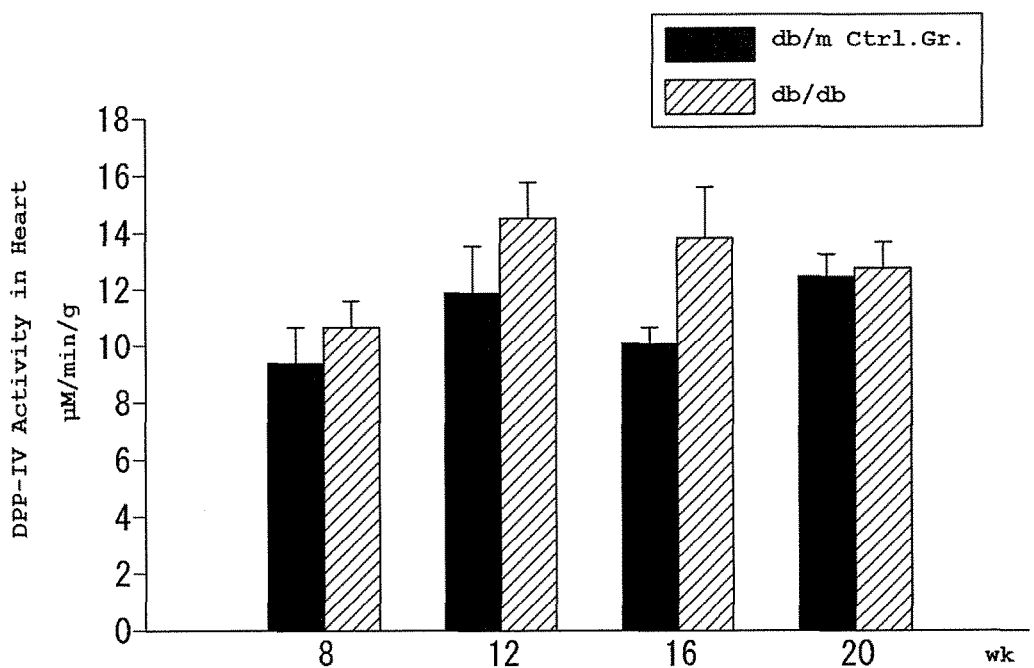
Figure 2D:
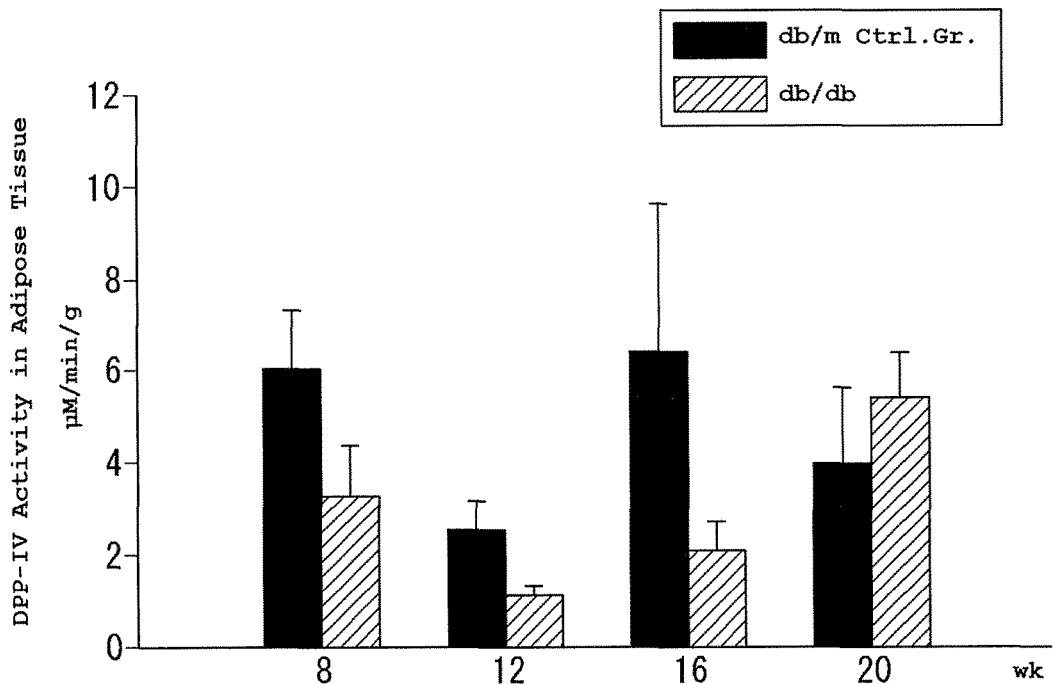
Figure 3A:
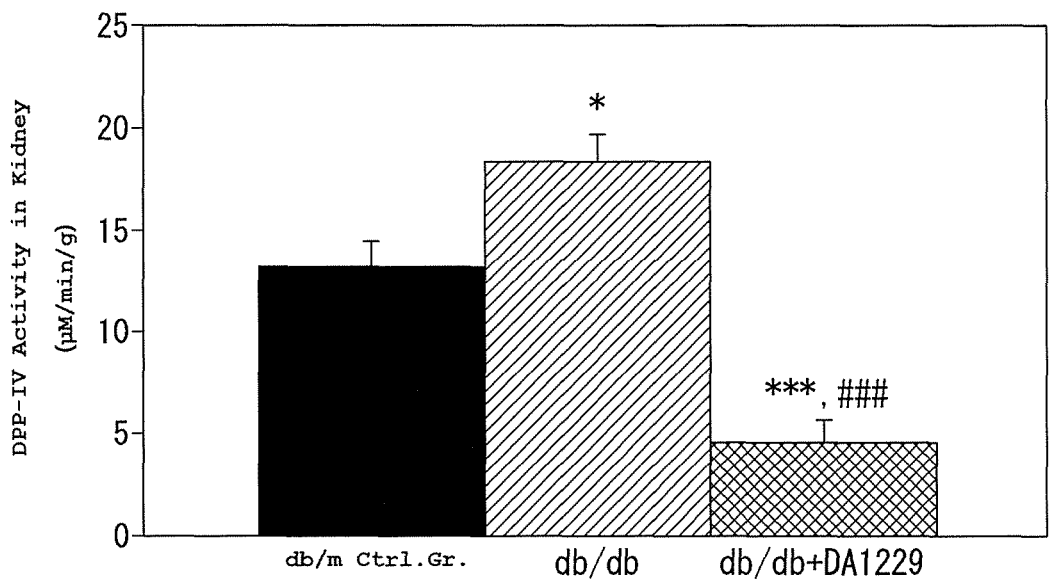
FIGS. 3A-3D show graphs demonstrating activity variation of DPP-IV in kidney (3A), liver (3B), heart (3C) and adipose tissue (3D) after administration of the DPP-IV inhibitor.
Figure 3B:
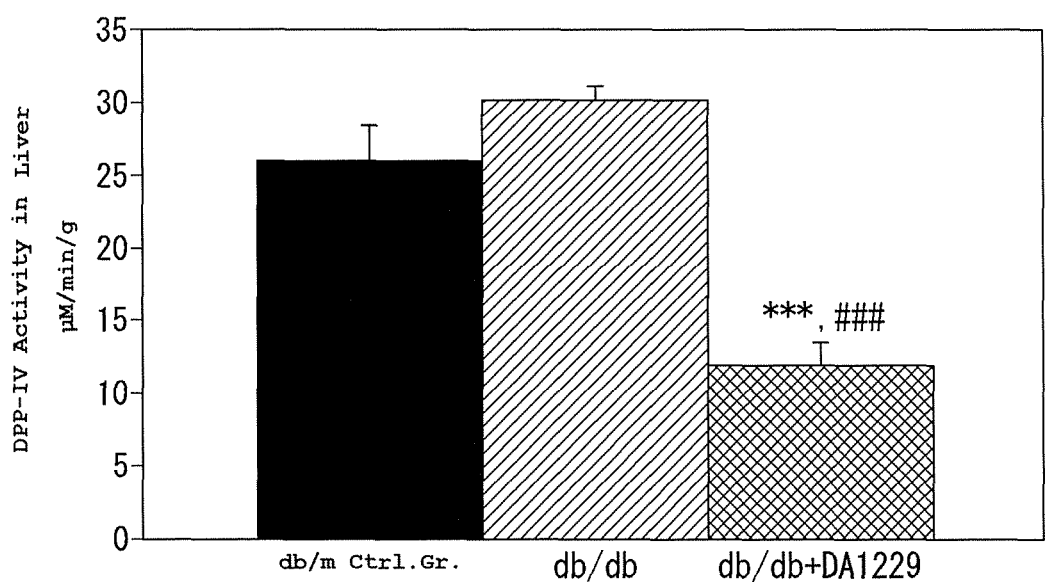
Figure 3C:
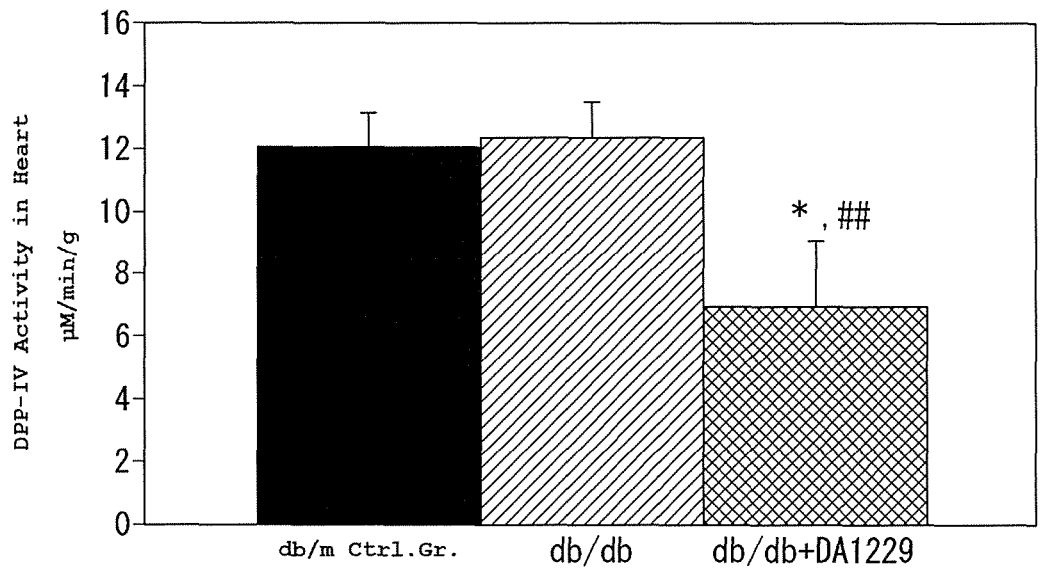
Figure 3D:
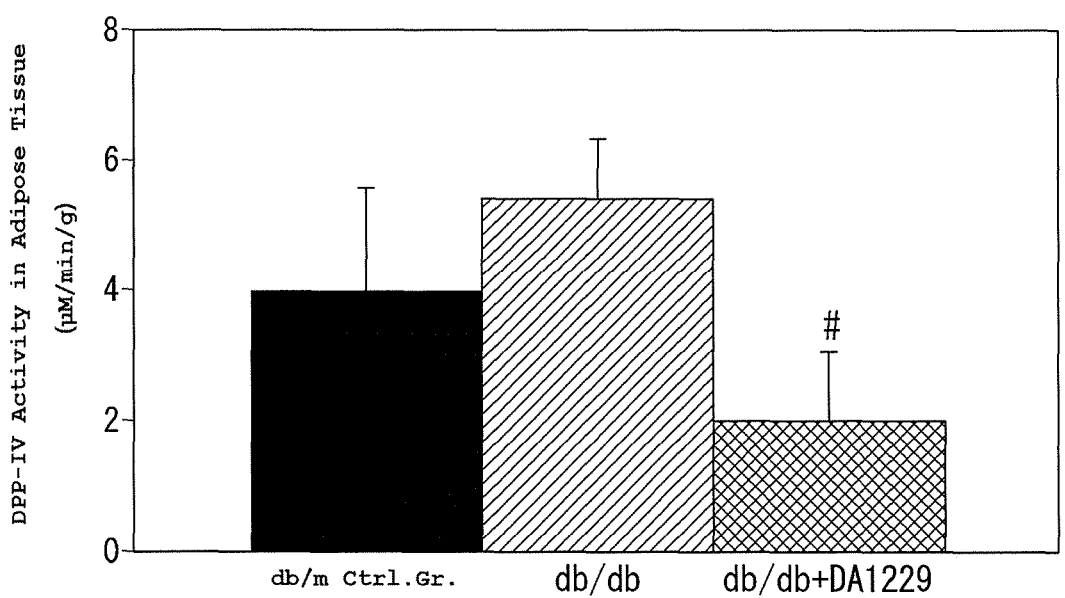

DPP-IV activity was measured by using fluorophotometric assay method (J. Med. Chem. 2005, 48, 141-151), which was reported previously. FIG. 1 shows DPP-IV activity in plasma. The non-diabetic control group and the diabetic group showed no significant difference in DPP-IV activity at each stage of diabetes progression (see FIG. 1A.) However, it was observed that DPP-IV activity was markedly decreased at $20^{th}$ week of administration in the DPP-IV inhibitor-administered group compared to the non-diabetic control group and the diabetic group (see FIG. 1B.)

FIG. 2 shows DPP-IV activity of each stage of diabetes progression in kidney, liver, heart and adipose tissue of the non-diabetic control group and the diabetic group. DPP-IV activity was shown to be high in each organ. Regarding the non-diabetic control group and the diabetic group, DPP-IV activities in liver, heart and adipose tissue were not very different compared to each other (see FIGS. 2B-2D) but in kidney, DPP-IV of the diabetic group was significantly increased as diabetes was progressed (see FIG. 2A.)

FIG. 3 shows DPP-IV activities in kidney, liver, heart and adipose tissue of the non-diabetic control group and the diabetic group and the DA1229 administration group at $20^{th}$ week of administration. DPP-IV activity in each organ of the DA1229 administration group was markedly decreased compared to that of the non-diabetic control group and the diabetic group, and this decrease was remarkable in kidney (see FIG. 3A.)

It could be understood from the above results that DA1229 inhibits DPP-IV activity in every organ and specifically, it effectively inhibits DPP-IV activity in kidney.

<Example 3> Evaluating Lipid Metabolism

In diabetic patients, blood lipids are tend to be increased and lipids are tend to be deposited in liver (i.e. hepatic steatosis) due to failure of lipid metabolism. Following experiment has been conducted to confirm whether DA1229 improves lipid metabolism. The non-diabetic control group, the diabetic group and the DA1229 administration group were prepared in the same manner as Example 1(1), and used for the experiment.
(1) Evaluating Blood Lipid Concentration Total cholesterol includes esterified cholesterol and non-esterified (free) cholesterol. Problems such as arteriosclerosis inter alia occur when concentration of LDL-cholesterol increases.

Concentrations of lipids, that are total cholesterol, triglyceride, HDL-cholesterol and LDL-cholesterol, of plasma of the non-diabetic control group, the diabetic group and the DA1229 administration group were measured at $12^{th}$ week of administration. Concentration of total cholesterol and triglyceride were measured by using a ELISA reader (Micro-Quant, Bio-Tek Instruments, Colmar, France) after using the GPO-Trinder kit (Sigma, St. Louis, Mo., USA); and HDL-cholesterol and LDL-cholesterol were measured by using a TBA-200FR NEO (Toshiba, Japan).

Figure 4:
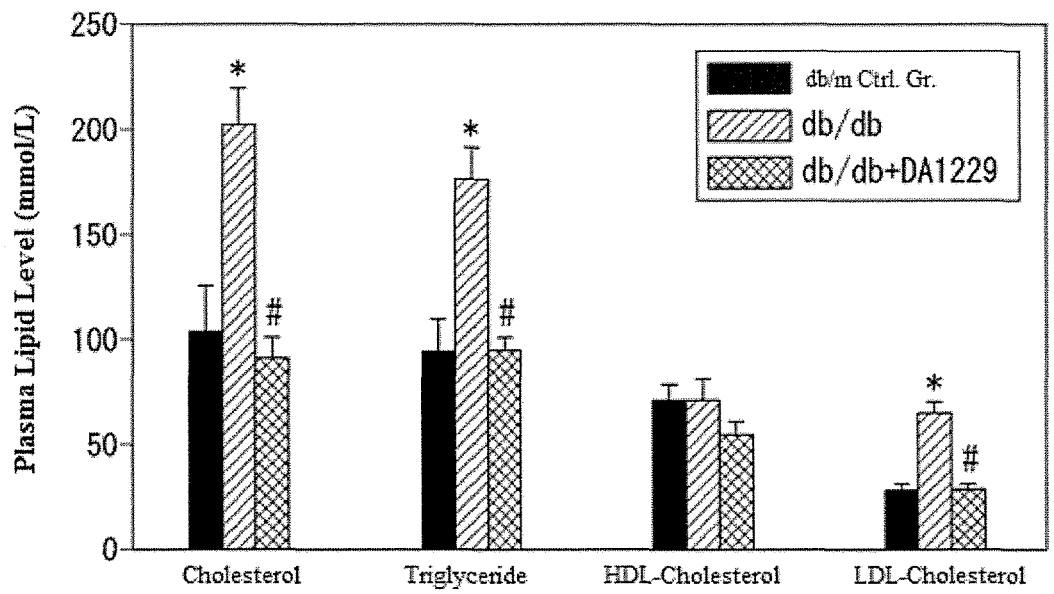
FIG. 4 shows a graph demonstrating the change of lipid metabolism after administration of the DPP-IV inhibitor.
Figure 5:
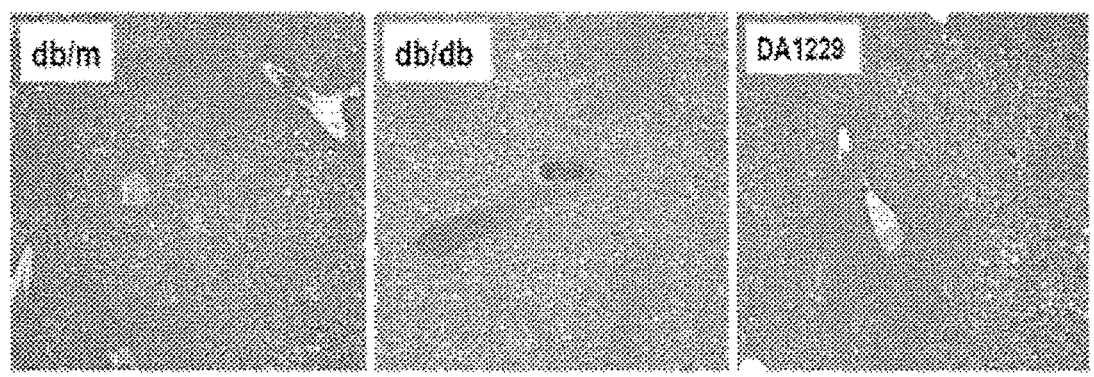
FIG. 5 illustrates a result of observation on hepatic steatosis after administration of the DPP-IV inhibitor.

Concentrations of total cholesterol, triglyceride and LDL-cholesterol in the diabetic group were increased approximately 2 times or more compared to the non-diabetic control group, but it was observed that this increase was restored to the level of the non-diabetic control group by administration of DA1229 (see FIG. 4).
(2) Evaluating Hepatic Steatosis Liver tissues collected from the non-diabetic control group, the diabetic group and the DA1229 administration group were sectioned by a microtome and embedded in paraffin after alcohol dehydration at $12^{th}$ week of administration. These sections were stained by Hematoxylin-eosin, and then lipid deposition was observed by using a microscope (STM6-LM Olympus NDT Inc, USA) (see FIG. 5). Lipid deposition of liver tissues was increased in the diabetic group compared to the non-diabetic control group, but it was observed that this increase was restored to the level of the non-diabetic control group in the DA1229 administration group.

It could be understood from the above result that DA1229 has an effect of increasing lipid metabolism that was decreased due to diabetes.

<Example 4> Evaluating Renal Function

Following experiment was conducted to confirm whether DA1229 administration improves renal function that was declined due to renal diseases. The non-diabetic control group, the diabetic group and the DA1229 administration group were prepared in the same manner as Example 1(1).
(1) Evaluating Plasma Creatinine Creatinine is a substance secreted by kidney and its concentration in plasma is shown to be high when there is a problem in kidney clearance.

TABLE 2

| Parameter | wk | db/m Ctrl.Gr. | db/db | db/db + DA1229 |
|---|---|---|---|---|
| Plasma Creatinine (μmol/L) | 12 | 35.0 ± 4.0 | 45.0 ± 6.0 | 29.0 ± 2.0† |

Each value was expressed as ± SEM in Table 2 and statistical analysis was conducted on each group in the same period.
†$P < 0.01$ vs. db/db.

Concentration of plasma creatinine was measured through the modified Jaffe method (Kang Y S et al., CCR2 antagonism improves insulin resistance, lipid metabolism, and diabetic nephropathy in type 2 diabetic mice. Kidney Int. 2010 November; 78(9):883-894, Kang Y S et al., Visfatin is upregulated in type-2 diabetic rats and targets renal cells. Kidney Int. 2010 July; 78(2):170-181) by using the TBA-200FR NEO (Toshiba, Japan.)

It was confirmed in Table 2 that plasma creatinine of the diabetic group was increased compared to the non-diabetic control group, and that of the DA1229 administration group was markedly decreased.
(2) Observation on Microalbuminuria When diabetes is progressed, phenomena of renal glomeruli destruction and protein (albumin) excretion incur, and microalbuminuria is directed to a case when the amount of the excretion is small. Microalbuminuria is one of the initial indices of renal diseases, and the gomeruli destruction becomes more severe as diabetes progresses. Accordingly the amount of protein excretion will increase. The non-diabetic control group, the diabetic group and the DA1229 administration group were prepared in the same manner as Example 1(1), and used for the experiment.

Microalbuminuria was observed by measuring the amount of urinary excretion of albumin during 24 hours in the non-diabetic control group, the diabetic group and the DA1229 administration group at week 0, 4, 8 and 12 of administration. The amount of albumin excretion was measured by using a ELISA reader (Micro-Quant, Bio-Tek Instruments, Colmar, France) after using the ELISA kit (Shibayagi, Shibukawa, Japan).

The amount of albumin excretion was increased in the diabetic group compared to the non-diabetic control group, and this increase became significant as diabetes progressed more. However, microalbuminuria was not observed in the DA1229 administration group until $4^{th}$ week. It was observed after $4^{th}$ week but the amount of urinary excretion of albumin was much smaller than that of the diabetic group (see FIG. 6).

It could be understood from the above result that protein excretion is decreased due to improvement of renal excretory function by administering DA1229.

<Example 5 Histological Evaluation on Renal Mesangial Expansion

Mesangial expansion incurs in kidney when renal destruction progresses in renal diseases. Therefore, glomerular mesangial expansion in the non-diabetic control group, the diabetic group and the DA1229 administration group was observed. An experiment was conducted with the non-diabetic control group, diabetic group and DA1229 administration group prepared in the same manner as Example 1(1), and observed at $12^{th}$ week of administration.

Renal glomerular tissues were collected and sectioned by a microtome and embedded in paraffin after alcohol dehydration. The sections were stained by using PAS (periodic acid-Schiff); observed by using a microscope (STM6-LM Olympus NDT Inc, USA) (see FIG. 7B); and scored by a pathologist (see FIG. 7A.)

Mesangial expansion was observed in the diabetic group compared to the non-diabetic control group but it was improved to a level close to the non-diabetic control group in the DA1229 administration group.

It could be understood from the above result that DA1229 improves renal glomeruli destruction.

<Example 6> Evaluating Renal Fibrosis

Renal diseases show a symptom of kidney destruction as renal diseases progresses due to deposition of fibrous proteins in kidney.

TGF β1 (Transforming Growth Factor β1) is cytokine inducing renal fibrosis, and Type IV collagen is a matrix forming fibrous tissues. PAI-1 (Plasminogen Activator Inhibitor-1) induces thrombosis. All of these 3 proteins are indices of renal fibrosis.

Following experiment was conducted to confirm whether DA1229 has an effect of inhibiting renal fibrosis. The experiment was conducted with the non-diabetic control group, diabetic group and DA1229 administration group prepared in the same manner as Example 1(1), and observed at $12^{th}$ week of administration.

(1) Histological Evaluation

Renal glomerular tissues were collected and sectioned by a microtome and embedded in paraffin after alcohol dehydration. The sections were stained via immunohistochemistry; each of deposited TGF β1, Type IV collagen and PAI-1 in kidney was observed by using a microscope (STM6-LM Olympus NDT Inc, USA) (see FIG. 8); and degree and range of the staining were scored by a pathologist (see FIG. 9).

Figure 8A:
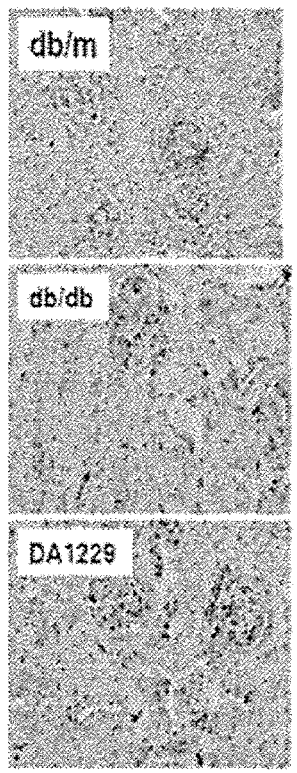
FIGS. 8A-8C illustrate deposition of renal fibrous protein (TGF β1, 8A; Type IV collagen, 8B; and PAI-1, 8C) after administration of the DPP-IV inhibitor.
Figure 9:
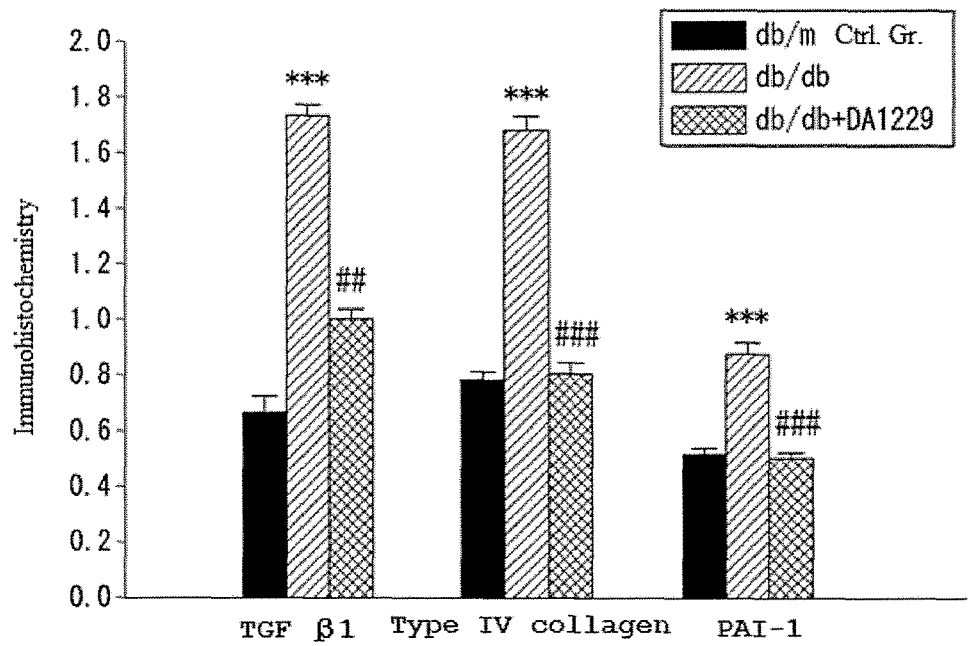
FIG. 9 is a graph showing the scoring of histological variation in FIG. 8.

TGF β1 in the diabetic group was increased compared to the non-diabetic control group but this effect was markedly decreased in the DA1229 administration group (see FIGS. 8A and 9).

Figure 8B:
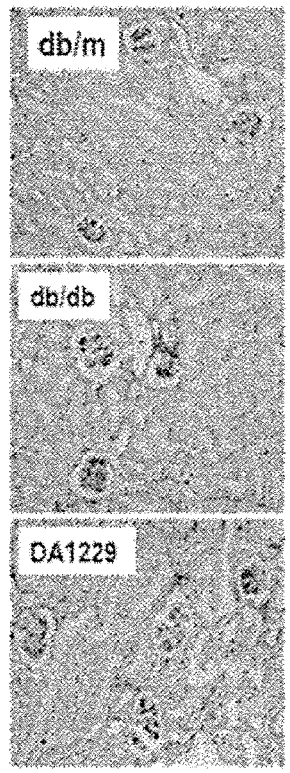

Type IV collagen in the diabetic group was increased compared to the non-diabetic control group but it was decreased to the level of the non-diabetic control group in the DA1229 administration group (see FIGS. 8B and 9).

Figure 8C:
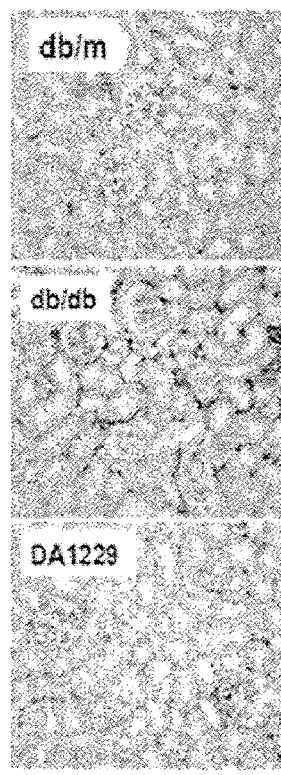

PAI-1 in the diabetic group was increased compared to the non-diabetic control group but it was decreased to the level of the non-diabetic control group in the DA1229 administration group (see FIGS. 8C and 9).

Figure 10:
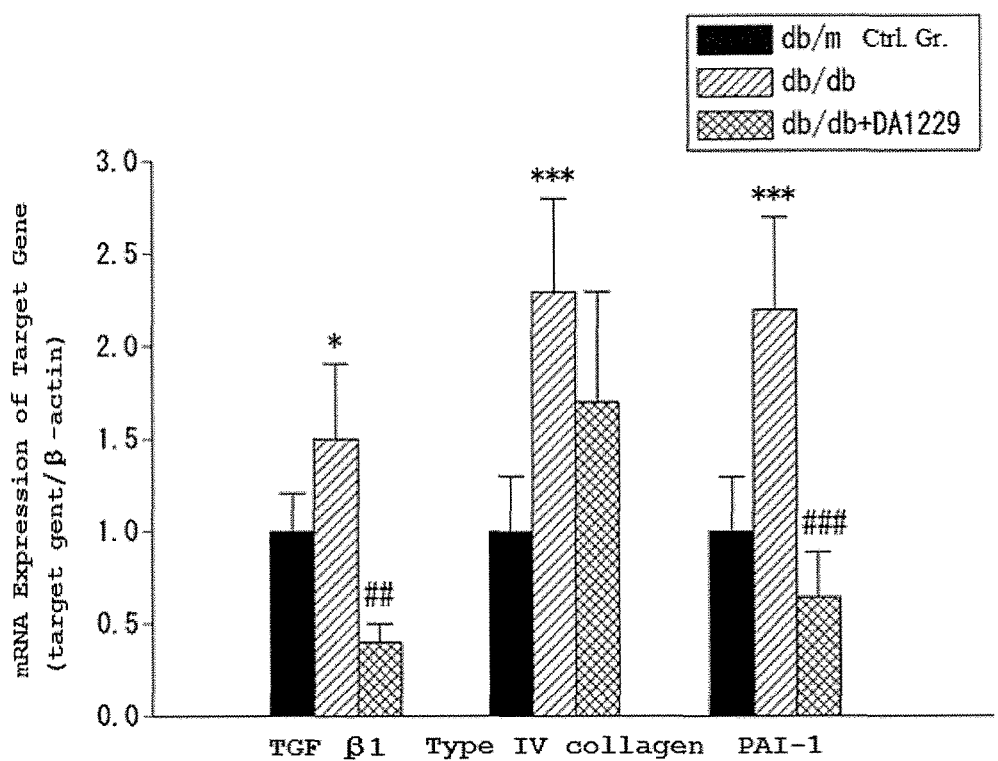
FIG. 10 is a graph showing expression of renal fibrous proteins after administration of the DPP-IV inhibitor.

(2) Evaluating Gene Expression mRNA expressions of TGF β1, Type IV collagen and PAI-1 were observed to see whether the decrease of fibrous proteins, which was confirmed in Example 6(1), occurs in the level of gene expression. mRNA was extracted from a renal tissue sample, and amplified in a PCR container containing SYBR Green reagent by using the Light Cycler 1.5 system (Roche Diagnostics Corporation, Indianapolis, Ind., USA) real-time PCR instrument. Values of expression level of each target gene in the diabetic group and the non-diabetic control group divided by expression level of β-actin were shown in FIG. 10.

mRNA expression of TGF β1 in the diabetic group was increased compared to the non-diabetic control group but it was markedly decreased in the DA1229 administration group.

mRNA expression of Type IV collagen in the diabetic group was increased two times or more compared to the non-diabetic control group but it was markedly decreased in the DA1229 administration group.

mRNA expression of PAI-1 in the diabetic group was increased two tithes or more compared to the non-diabetic control group but it was markedly decreased in the DA1229 administration group.

It could be understood from the above results that DA1229 exhibits excellent effects in inhibiting renal fibrosis.

<Example 7> Evaluating Renal Lipid Metabolism

Figure 11:
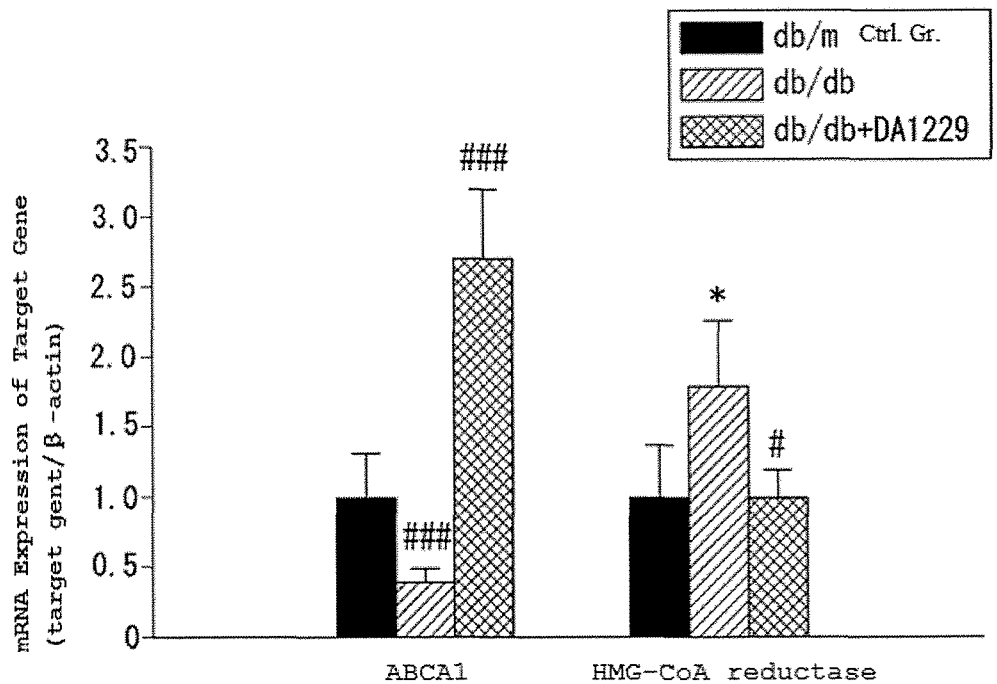
FIG. 11 is a graph showing expression of renal lipid metabolism proteins after administration of the DPP-IV inhibitor.
Figure 12:
FIG. 12 illustrates PCR result of renal lipid metabolism proteins after administration of the DPP-IV inhibitor.

ABCA1 is a protein involved in lipid excretion from tissues, and HMG-CoA reductase is a protein involved in lipid synthesis.

mRNA expressions of ABCA1 gene and HMG-CoA reductase gene were observed to see whether lipid metabolism in kidney was decreased and whether this phenomenon was improved by administration of DA1229. The experiment was conducted with the non-diabetic control group, diabetic group and DA1229 administration group prepared in the same manner as Example 1(1), and observed at $12^{th}$ week of administration.

mRNA was extracted from the renal tissue sample and amplified in the PCR container containing SYBR Green reagent by using the Light Cycler 1.5 system (Roche Diagnostics Corporation, Indianapolis, Ind., USA) real-time PCR instrument. The result is shown in FIGS. 11 and 12.

mRNA expression of ABCA1 in the diabetic group was decreased compared to the non-diabetic control group but it was markedly increased in the DA1229 administration group.

mRNA expression of HMG-CoA reductase in the diabetic group was increased compared to the non-diabetic control group but it was decreased to the level of the non-diabetic control group in the DA1229 administration group.

It could be understood from the above result that DA1229 inhibits deposition of lipid in renal tissues and decreases lipid synthesis.

<Example 8> Evaluating Effects on Nephrin Excretion and Nephrin Expression Nephrin is a protein expressed on cell membrane of podocyte which forms glomerular filtration membrane.

Nephrin forms a filtration barrier by binding to adjacent podocyte. When proteinuria incurs due to glomerular damage, nephrin barrier is damaged because nephrin expression in podocyte decreases, and accordingly, urinary excretion of nephrin increases. Therefore, urinary excretion of nephrin and nephrin expression in kidney in the non-diabetic control group, the diabetic group and the DA1229 administration group were observed. The non-diabetic control group, the diabetic group and the DA1229 administration group were prepared in the same manner as Example 1(1), and used for the experiment.

(1) Evaluating Nephrin Excretion

Figure 13A:
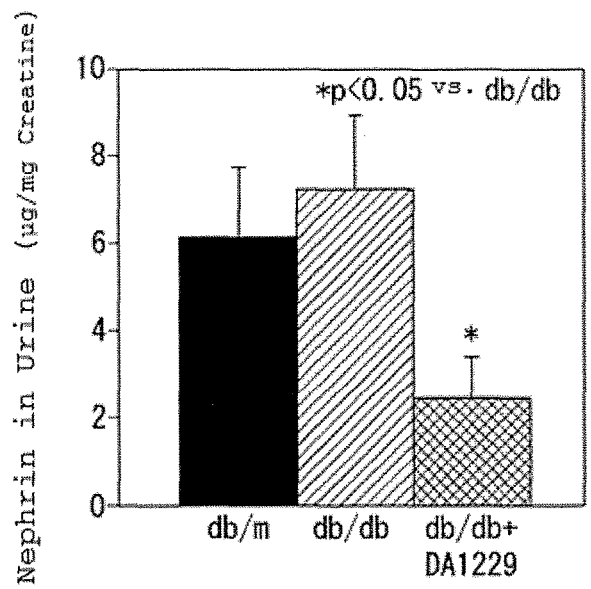
FIG. 13A shows urinary excretion of nephrin after administration of the DPP-IV inhibitor in a mouse model of diabetic nephropathy.
Figure 13B:
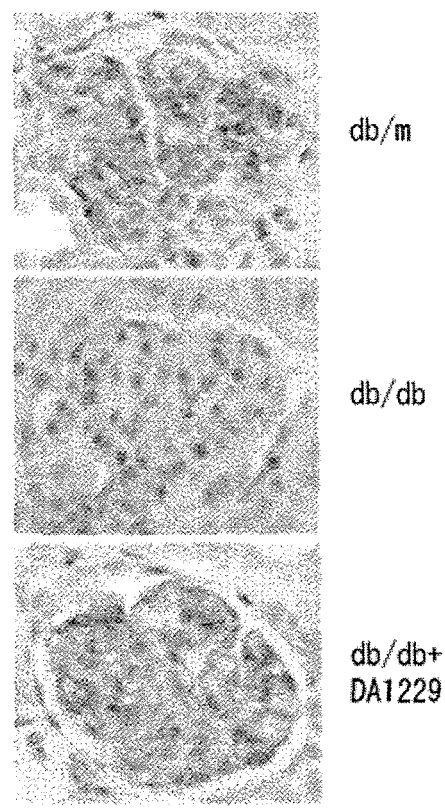
FIG. 13B illustrates effects of the DPP-IV inhibitor on nephrin expression of renal glomeruli, which was observed through immunostaining.

Urine of each non-diabetic control group, diabetic group and DA1229 administration group was collected and nephrin content in urine was quantified by using the EIA kit (Exocell Inc. Philadelphia, Pa., USA). It was then normalized by creatinine excretion, which is proportional to a volume of urination (measured by the modified Jaffe method) and shown in the left-hand side graph in FIG. 13. As shown in the graph, it was confirmed that content of nephrin in urine was increased in the diabetic group compared to the non-diabetic control group but markedly decreased in the DA1229 administration group.

(2) Evaluating Nephrin Expression

In addition, kidneys were isolated from each group; renal tissues were separated, immunostained with nephrin-specific antibody, and observed by using a microscope. Result is shown in right-hand side of FIG. 13. It is shown that observed nephrin was few in the diabetic group compared to the non-diabetic control group, but much in the DA1229 administration group.

It could be understood from the above result that glomerular structure was maintained due to preservation of glomerular nephrin barrier, and urinary excretion of nephrin was decreased.

<Example 9> Observing Microalbuminuria in a Non-Diabetic Renal Disease Mouse Model and Evaluating Effects on Nephrin Excretion Following experiment was conducted to confirm effect of DA1229 on kidney irrespectively of blood glucose level or diabetes by preparing a non-diabetic renal disease mouse model.

(1) Preparation of the Non-Diabetic Renal Disease Mouse Model

Non-diabetic renal diseases occurs via induction of glomerular podocyte damage when injecting adriamycin (hereinafter, ADX) that is an anti-cancer agent.

Thirty mice at the age of 6 weeks were divided into 3 groups (n=10/group) after single intravenous injection of 13 mg/kg of ADX. For the first group, the administration of DA1229 was initiated immediately and maintained while renal disease incurred and developed. For the second group, administration of DA1229 was performed 3 weeks after single ADX injection, for the purpose of administering DA1229 after renal disease was progressed to some degree. The third group was set as a control group without any additional action. DA1229 was administered as a mixture with diet at 0.3% (W/W, 300 mg/kg/day) to the first and second groups. Only feed was provided to the control group. Microalbuminuria and nephrin excretion of each group were measured at $5^{th}$ week of administration.

(2) Observing Microalbuminuria and Evaluating Effects on Nephrin Excretion

Microalbuminuria (i.e. albumin in urine) of the first through third group were observed at $3^{rd}$ week of administration in the same manner as the method stated in Example 4(2), and effects on urinary excretion of nephrin was evaluated in the same manner as the method stated in Example 8.

Figure 14A:
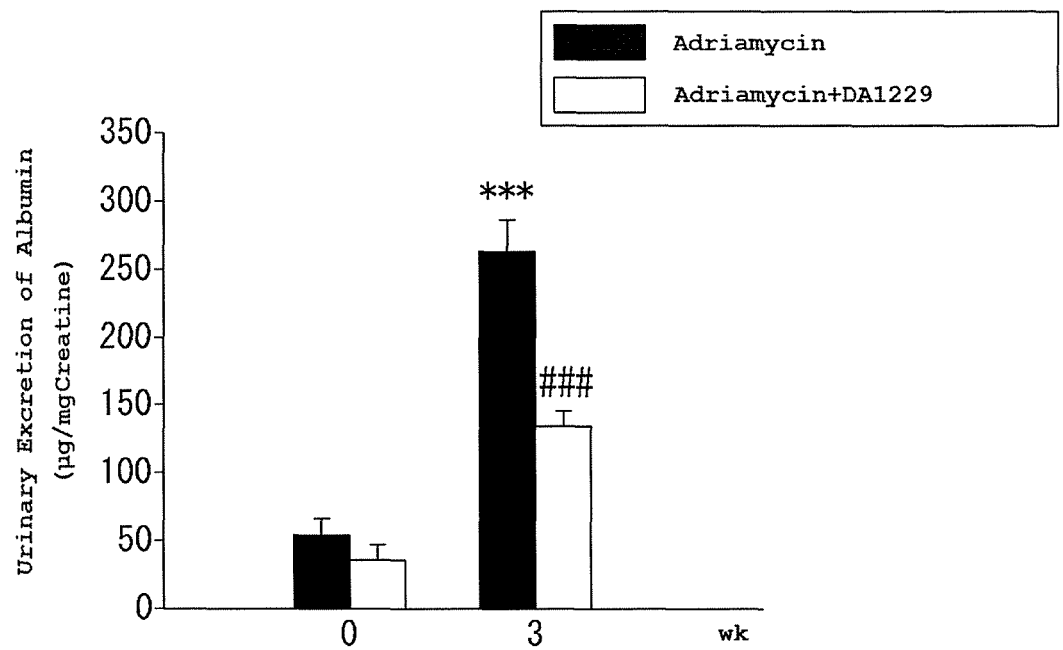
FIG. 14A shows a graph demonstrating effects on microalbuminuria and FIG. 14B shows a graph of urinary nephrin excretion upon induction of renal diseases and administration of the DPP-IV inhibitor at the same time to a mouse model of non-diabetic nephropathy.
Figure 14B:
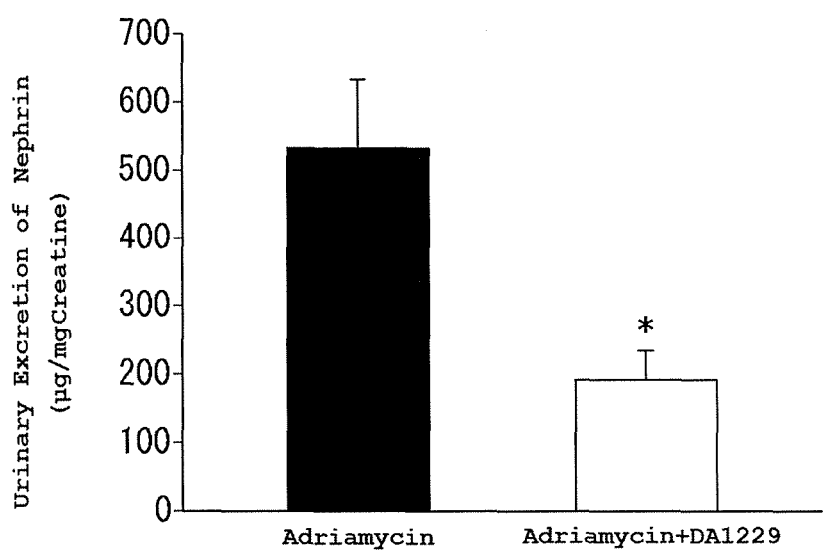

Result of the first group wherein induction of renal disease and administration of DA1229 were simultaneously performed was shown in FIG. 14 (the black bars correspond to the third group i.e. the control group; and the white bars correspond to the first group). It was confirmed in FIG. 14 that both urinary excretion of albumin (A) and urinary excretion of nephrin (B) were significantly decreased by administration of DA1229.

Figure 15A:
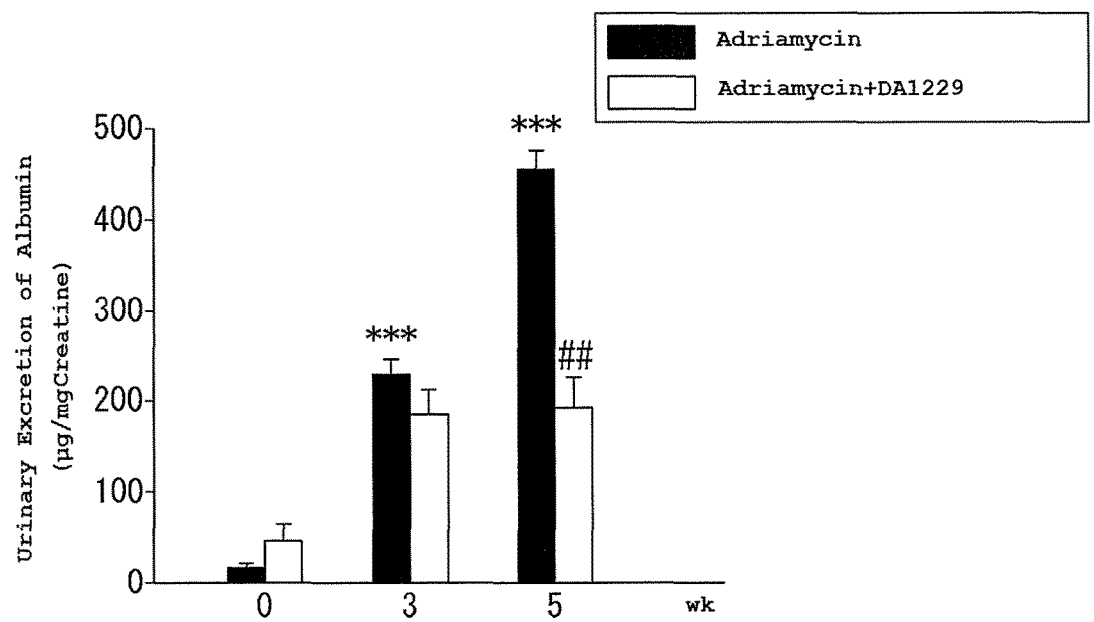
FIG. 15A shows a graph showing effects on microalbuminuria and FIG. 15B shows a graph of urinary nephrin excretion upon inducing renal diseases and then administering the DPP-IV inhibitor to the mouse model of non-diabetic nephropathy.
Figure 15B:
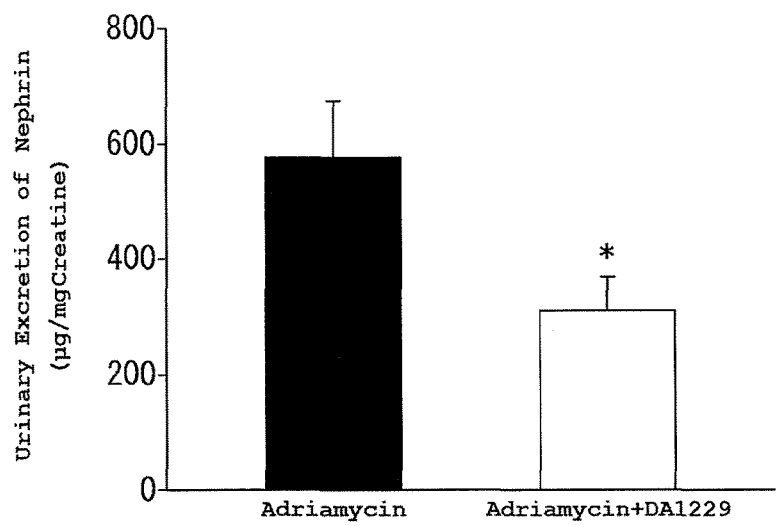

Result of the second group wherein administration of DA1229 was performed after induction of renal disease was shown in FIG. 15 (the black bars correspond to the third group i.e. the control group; and the white bars correspond to the first group.) It was confirmed in FIG. 15 that both urinary excretion of albumin (A) and urinary excretion of nephrin (B) were significantly decreased by administration of DA1229. It was confirmed in the upper side of FIG. 15 that effect of decreasing albumin excretion by DA1229 became more significant as time passed.

It could be understood from the above results that DA1229 has an effect of protecting glomerulus in renal disease that is caused by non-diabetic glomerular damage as well as diabetic renal diseases.

<Example 10> Evaluating DPP-IV Expression of Renal Cells Upon Occurrence of Stimulation from Diabetes Following experiment was conducted to confirm whether DPP-IV gene expression increased in cells forming kidney by stimulation occurring in diabetes.

High glucose (30 mM), 100 nM of angiotensin II or 100 μM of free fatty acid (i.e. palmitic acid), which are similar to the stimuli occurring in diabetes, were added for 48 hours to podocyte, proximal tubule cell and mesangial cell, which are cells forming renal tissues; and then DPP-IV gene expression was observed. Total RNA was extracted from samples obtained from each cell, and mRNA was amplified in the PCR container containing SYBR Green reagent by using the Light Cycler 1.5 system (Roche Diagnostics Corporation, Indianapolis, Ind., USA) real-time PCR instrument.

Figure 16:
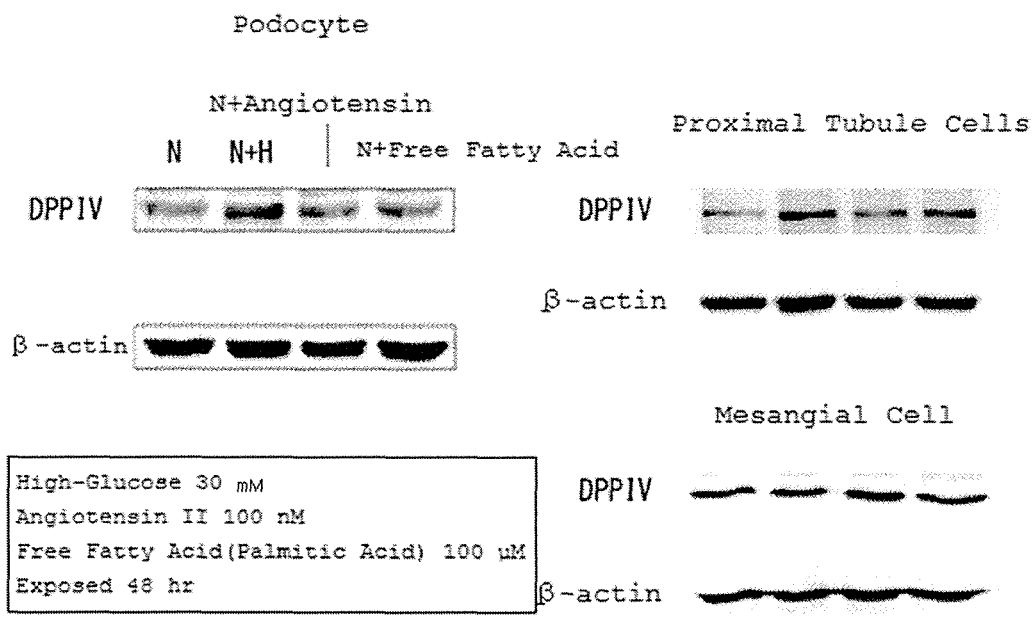
FIG. 16 illustrates a result of an observation on expression of DPP-IV gene upon stimulating renal podocytes, proximal tubule cells and mesangium cells with high-glucose, angiotensin II and fatty acid.

Increase of DPP-IV gene expression was not observed in mesangial cell, but it was observed in podocyte and proximal tubule cell (see FIG. 16.) It could be understood from the above result that expression of DPP-IV of renal cells including podocyte increases in diabetic renal diseases.

<Comparative Example> Comparison on Renal Protective Effects Among DA1229 and Other DPP-IV Inhibitors Renal protective effect of DA1229 was compared to those of other DPP-IV inhibitors, such as linagliptin, saxagliptin, and sitagliptin.

(1) Comparison on Effects of DPP-IV Inhibiting Activity in Podocyte

Podocytes were cultured for 72 hours in media containing DA1229, linagliptin, saxagliptin or sitagliptin in concentration of 0 nM, 1 nM, 10 nM and 100 nM respectively. After that, the media were removed; podocytes were washed with phosphate buffer; and DPP-IV activity was measured in the same manner as Example 2 by using the fluorophotometric assay method as that was reported previously (J. Med. Chem. 2005, 48, 141-151.)

Figure 17:
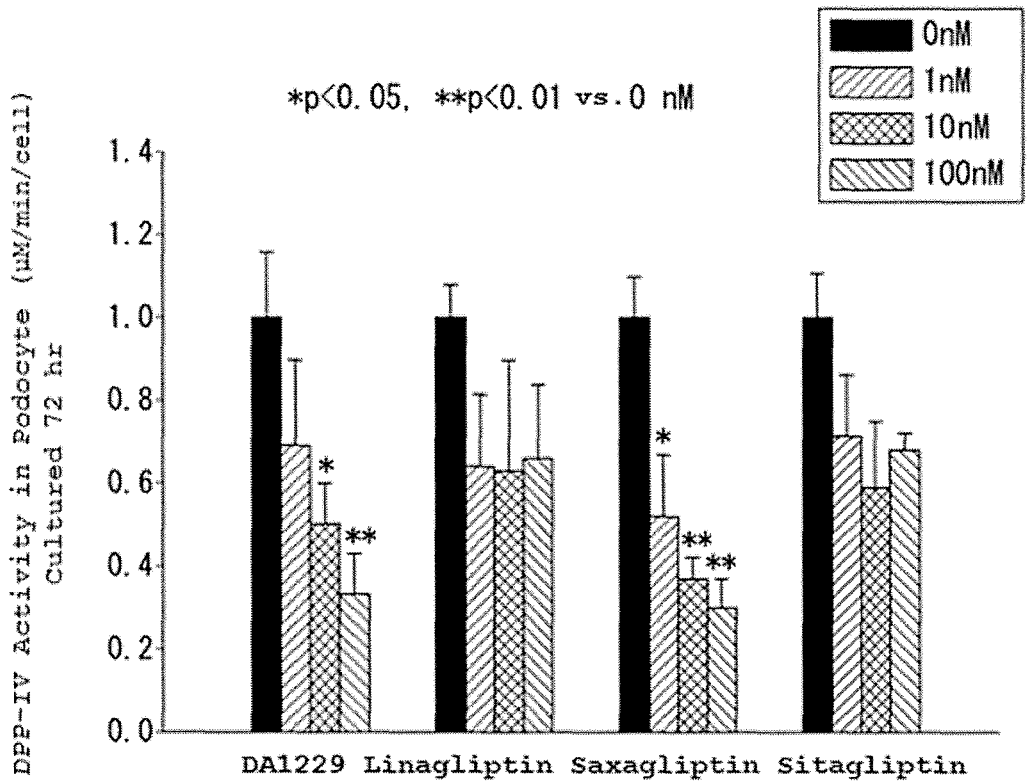
FIG. 17 is a graph showing comparison of DPP-IV activity-inhibiting effects between conventional DPP-IV inhibitors (linagliptin, saxagliptin and sitagliptin) and the DPP-IV inhibitor of the present disclosure.

It is shown in FIG. 17 that DA1229 inhibits DPP-IV activity in podocytes in a dose-dependent manner; and its effect is superior to that of linagliptin and sitagliptin, and similar to that of saxagliptin.

(2) Comparison on Effects on Nephrin Expression Upon Same Stimuli as Diabetes

Effects of DA1229, linagliptin, saxagliptin and sitagliptin on nephrin expression under stimuli of glucose and angiotensin II that are same to the stimulation occurring in diabetes were observed below.

Podocytes were cultured for 72 hours in media containing 30 mM of glucose, 100 nM of angiotensin II; and any one of 10 nM of DA1229, 10 nM of linagliptin, 1 nM of saxagliptin and 10 nM of sitagliptin. After that, the media were removed; cells were lysed; and changes of intracellularly expressed nephrin were measured through western blot by using polyclonal antibody (Santa Crúz, SC-19000.)

Figure 18:
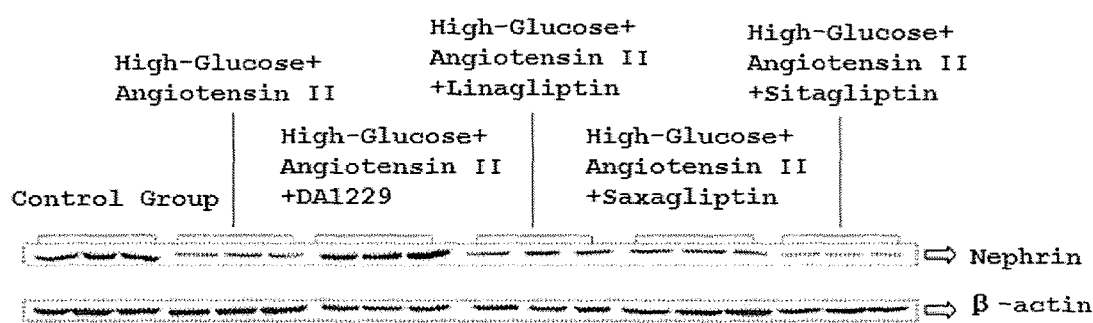
FIG. 18 illustrates effects of the conventional DPP-IV inhibitors (linagliptin, saxagliptin and sitagliptin) and the DPP-IV inhibitor of the present disclosure on nephrin expression upon stimulating renal podocytes with high-glucose and angiotensin II.

It is confirmed in FIG. 18 that nephrin expression is decreased due to glucose and angiotensin II treatment (the second left) compared to the control group treated with normoglucose (NG, the first left), but nephrin expression is maintained equally to the control group by DA1229 (the third left.) Meanwhile, nephrin expression of groups treated with linagliptin or saxagliptin was higher than the group treated only with glucose and angiotensin II, but much lower than the group treated with DA1229, and nephrin expression of the group treated with sitagliptin had almost no difference compared to the group treated only with glucose and angiotensin II.

It could be understood from the above result that DA1229 has superior renal DPP-IV inhibitory effect to that of commercially available conventional DPP4 inhibitors, i.e. linagliptin, saxagliptin and sitagliptin; and has superior effect of maintaining nephrin expression in renal glomeruli even under stimuli same to those occurring in diabetes.

INDUSTRIAL APPLICABILITY

The pharmaceutical composition of the present disclosure for preventing or treating renal diseases improves lipid metabolism, prevents histological damage including renal fibrosis, alleviates microalbuminuria, and maintains nephrin of renal glomeruli. Therefore, the composition is useful for treating renal diseases.

The invention claimed is:

1. A method of treating a renal disease in a subject who does not have diabetes, comprising:
    administering to the subject who has the renal disease who does not have diabetes a pharmaceutical composition comprising a therapeutically effective amount of a compound of Formula 1:

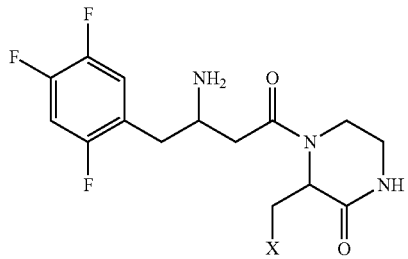

or a pharmaceutically acceptable salt thereof, wherein:
    X is $OR^1$ and $R^1$ is tert-butyl; and
    the renal disease is a glomerulonephritis.

2. The method of claim 1, wherein the pharmaceutically acceptable salt is selected from the group consisting of acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluenesulfonic acid and adipic acid.

3. The method of claim 1, wherein the pharmaceutical composition further comprises an angiotensin converting enzyme inhibitor or an angiotensin II receptor blocker, wherein:
    the angiotensin converting enzyme inhibitor is selected from the group consisting of captopril, enalapril, benazepril, imidapril, lisinopril, prinopril, ramipril, moexipril, fosinopril and quinapril; and
    the angiotensin II receptor blocker is selected from the group consisting of candesartan, eprosartan, irbesartan, losartan, telmisartan and valsartan.

* * * * *